Figure 1:
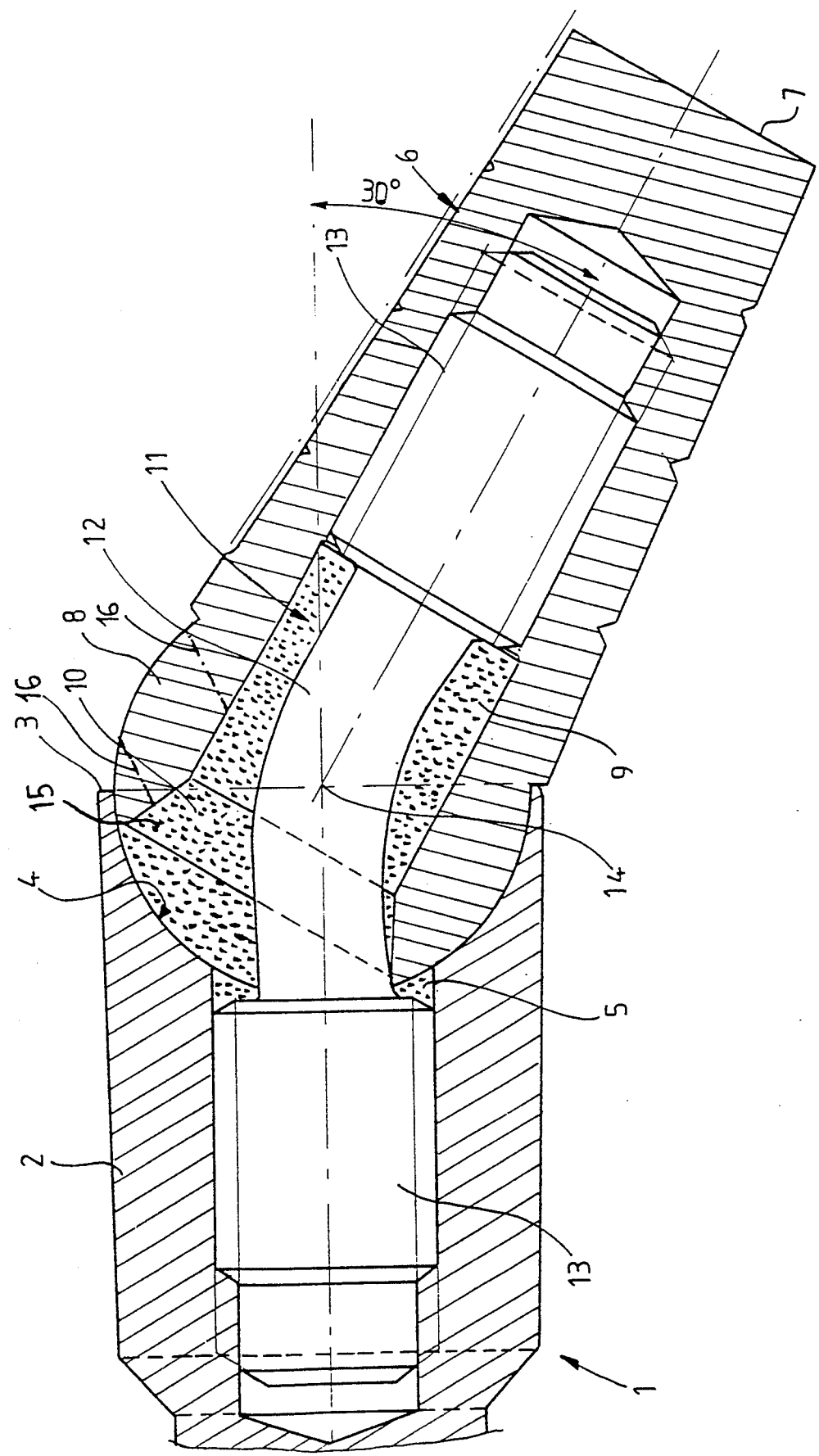

United States Patent [19]
Peltier et al.

[11] Patent Number: 5,178,539
[45] Date of Patent: Jan. 12, 1993

[54] DENTAL IMPLANT

[76] Inventors: Patrick Peltier; Guy Peltier, both of 57 Rue Des Lilas, 92500 Rueil Malmaison, France

[21] Appl. No.: 688,535
[22] PCT Filed: Dec. 4, 1990
[86] PCT No.: PCT/FR90/00876
  § 371 Date: Jun. 17, 1991
  § 102(e) Date: Jun. 17, 1991
[87] PCT Pub. No.: WO91/08714
  PCT Pub. Date: Jun. 27, 1991

[30] Foreign Application Priority Data
Dec. 12, 1989 [FR] France .................. 89 16385

[51] Int. Cl.⁵ .............................. A61C 8/00
[52] U.S. Cl. ....................... 433/173; 433/176
[58] Field of Search ........... 433/173, 174, 175, 176

[56] References Cited

U.S. PATENT DOCUMENTS

| | | | |
|---|---|---|---|
| 3,732,621 | 5/1973 | Bostrom | 433/173 |
| 4,276,026 | 6/1981 | Edelman | 433/176 |
| 4,645,453 | 2/1987 | Niznick | 433/173 |
| 4,713,004 | 12/1987 | Linkow et al. | 433/174 |
| 4,758,161 | 7/1988 | Niznick | 433/173 |
| 4,793,808 | 12/1988 | Kirsch | 433/173 |
| 4,832,601 | 5/1989 | Linden | 433/173 |
| 4,842,518 | 6/1989 | Linkow et al. | 433/174 |
| 4,907,969 | 3/1990 | Ward | 433/173 |
| 4,932,868 | 6/1990 | Linkow et al. | 433/174 |
| 5,007,835 | 4/1991 | Valen | 433/174 |
| 5,030,095 | 7/1991 | Niznick | 433/173 |
| 5,073,110 | 12/1991 | Barbone | 433/173 |

Primary Examiner—Cary E. O'Connor
Attorney, Agent, or Firm—Larson and Taylor

[57] ABSTRACT

A dental implant comprises an insert member received into the jaw and an implant head connected thereto. The insert member has a straight part, the end of which is flush with the surface of the jaw when the member is inserted into the jaw. The implant head is detachably connected to the insert member and a dental prosthesis is mounted thereon. The insert member and the implant head are innerconnected by a ball joint permitting angular orientation of the implant head relative to the insert member. A bendable connector element connects the implant head to the insert member by extending through cavities located therein, the connector element being bendable, in the vicinity of the center of the ball joint.

13 Claims, 2 Drawing Sheets

DENTAL IMPLANT

The invention relates to dental implants for implanting in the lower or upper jaw to serve as a support for a dental prosthesis, crown or bridge, after the total extraction of one or more teeth. Generally, these implants are formed by a member insertable in the bony tissue and a head, termed implant head, which is fixed on the insertable member and receives the prosthesis.

U.S. Pat. No. 3,732,621 describes a dental implant in which the head and the insertable member are interconnected by a ball joint to permit the inclination of the head with respect to the insertable member. The locking in position is ensured by a lock screw or by putting a flexible tie such as a cable under tension. The dental implant described in this document has a relatively complicated structure.

There has also been proposed (U.S. Pat. No. 4,758,161; U.S. Pat. No. 4,276,026 and U.S. Pat. No. 4,645,453) an implant head in a single piece having a thinning down permitting the bending of said head. The requirements of strength and rigidity limit the thinning down and this imposes the bending of the head outside the mouth and may consequently render the mounting of such a head in an implant located between two teeth impossible because of the clearance required when screwing the bent head. Further, a part of the head, i.e. the base, is not bent, which in particular has a disadvantageous repercussion on the construction of the prosthesis.

The invention therefore has for object to remedy the drawbacks mentioned hereinbefore by providing a dental implant capable of being suitably angularly and circumferentially disposed. Another object of the invention is to provide such a dental implant which is easy to produce and use.

The invention therefore provides a dental implant for implanting in the lower or upper jaw to serve as a support for a dental prosthesis and comprising a member, such as a screw-threaded stem, blade or the like, which is insertable in the bony tissue of the receiving jaw so as to ensure the anchoring of the implant and which comprises a straight, in particular cylindrical, part an end of which is flush with the surface of the jaw when said member is inserted in the latter, and an implant head which is detachably connected to said member and on which the dental prosthesis is mounted, in which implant the insertable member and the head are interconnected by a ball joint allowing the orientation of the head with respect to the insertable member so as to permit the suitable angular and circumferential positioning of the head with respect to the receiving jaw and in which there are provided means for ensuring the immobilization of the head in said suitable position and, in the straight part of the insertable member, a cylindrical cavity extending concentrically with the longitudinal axis of said part and prolonged into the head through a second cylindrical cavity, concentric with the longitudinal axis of the head, said implant being essentially characterized in that there is provided in said cavities an element which connects the head to the insertable member and is bendable, in the mouth, in the vicinity of the center of the ball joint. Bendable element is intended to mean an element which itself retains the shape, i.e. the inclination, imparted thereto by bowing.

Preferably, when finally mounting the head, the cavities in the insert member and implant head, at least in the vicinity of the ball joint are filled with a dental cement, or other material, capable of being broken up by suitable means, in particular by ultrasonic waves, for a possible dismounting of the head. Particularly appropriate cements are the cements containing zinc phosphate and, generally, all cements which do not "weld" the metal from which the implant is made.

Preferably, the head comprises at one of its ends a spherical part which is so arranged as to be closely cooperative with a complementary contact surface, in the shape of a part of a hollow sphere, carried by said flush end of the insertable member, the spherical part and the surface of contact constituting said ball joint. The included angle of the opening of the spherical surface of contact, i.e. the angle defined by the two most remote radii passing through the center of an imaginary circle in which the surface of contact is inscribed, is at the most equal to 180° so as to render the connection detachable. It is preferred that this angle be equal to 180° for reasons of strength and therefore that the surface of contact be a hollow semi-sphere.

Preferably, the cavities provided in the straight part of the insertable element and in the implant head in the extension of each other, are internally screw-threaded in at least a part of their length, the bendable element comprises a bendable rod carrying at, or close to, each of its ends, a satellite provided with a screw thread which is complementary to that of the corresponding cavity and, at the free end of the spherical part of the implant head, the cavity provided in the implant head widens in a frustoconical manner, the ball joint, the cavities and the bendable rod being so dimensioned as to be capable of sustaining an inclination, of the implant head relative to the straight part of the insertable member, of about 0° to 30°.

After bending, the bendable element is advantageously symmetrical with respect to its center so as to facilitate the work of the practitioner. The screw-threaded parts of each cavity are therefore equivalent.

Preferably, the dental implant according to the invention is wholly made from pure titanium of a dental grade. It is also possible to envisage making it from a titanium, aluminium and vanadium alloy.

Figure 2:
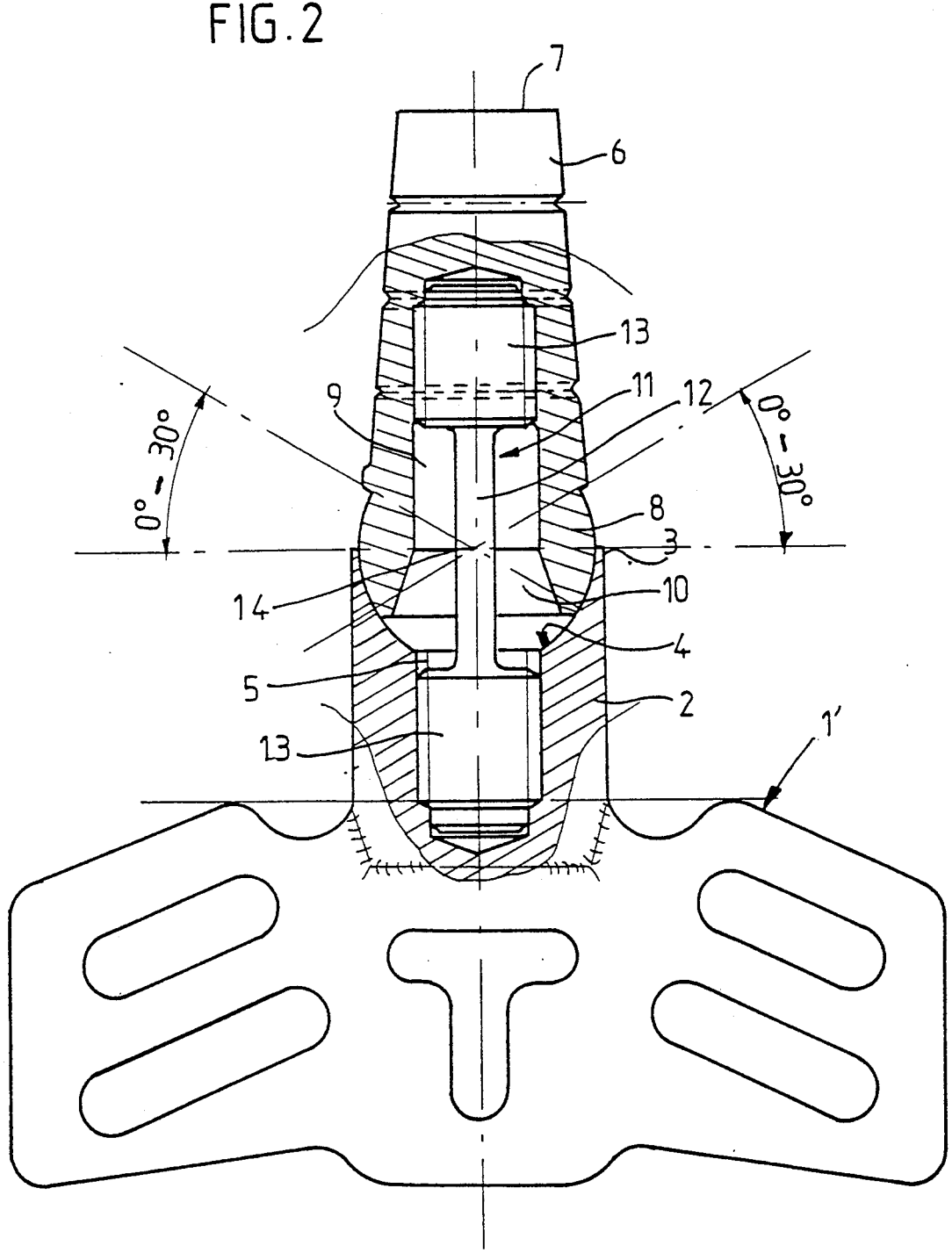

The invention will now be described in more detail with the aid of embodiments chosen as non-limitative examples and with reference to the accompanying drawing in which:

FIG. 1 shows, partly in longitudinal median section, the implant head and a part of a stem of a screw-implant according to an embodiment of the invention, FIG. 2 shows the same embodiment as shown in FIG. 1 for a blade-implant.

The dental implant according to the invention is made from pure titanium of dental grade and comprises a member insertable in the jaw of the patient. In FIG. 1, which concerns a screw-implant, the insertable member is a cylindrical member or stem 1 which is partly shown and comprises a usual screw-threaded part and a non-screw-threaded part 2 the end of which is flush with the surface of the jaw or of the gum when the stem 1 is in position. In FIG. 2, which concerns a blade-implant, the cylindrical member is replaced by a usual blade 1', in particular an apertured blade, which is extended by a part 2 identical to the non-screw-threaded part 2 of FIG. 1. At its end 3 remote from the screw-threaded part or from the blade proper, the part 2 of the insertable member 1 or 1' has a surface in the shape of a hollow semi-sphere, termed surface of contact 4. The part 2 further comprises a cylindrical cavity 5 extending in substantially the entire length of said part 2 and concentrically with the longitudinal axis of the latter. The cavity 5 is internally screw threaded.

The implant further comprises an implant head 6 which is the part of the implant located outside the jaw and receives the prosthesis. This implant head 6 has a generally frustoconical shape with a narrow end 7 and a partly spherical end, termed in this context "spherical part" 8. More precisely, this spherical part 8 is a spherical segment whose median axis coincides with the longitudinal axis of the implant head 6. The implant head 6 has an axial cavity 9 which opens onto the spherical part 8 through an outwardly divergent frustum of a cone 10. The axial cavity 9 has an internal screw thread.

The surface of contact 4 and the spherical part 8 are so dimensioned as to be capable of forming a ball joint in which the outer surface of the spherical part 8 closely cooperates with the surface of contact 4, when the implant head 6 and the member 1 or 1' are assembled. The implant head 6 and the member 1 or 1' are assembled by means of an oblong element 11 which is screwed into each of the cavities 5 and 9 and comprises a rod 12 provided, at each of its ends, with a satellite 13 including a screw thread which is complementary to the internal screw thread of the cavities 5 and 9. The oblong element 11 is symmetrical relative to the center 14 of the rod 12. When the implant is assembled, the center 14 coincides with the center of the ball joint.

For mounting the implant head 6 on the insertable member 1 which has been placed in position in the jaw of the patient, the rod 12 is screwed fully into the implant head 6. The practitioner then presents the implant head 6—rod 12 assembly after having put a suitable dental cement 15 (which is capable of being broken up by ultrasonic waves) on the end of said implant head 6, in particularly in the cavity formed by the frustum of a cone 10, then screws the implant head 6 in the insertable member 1 without fully locking it. He then effects the required bending with the aid of a suitable tool, then screws the implant head home. The cement in excess emerging from the ball joint is then removed.

The bending angle is limited by the configuration of the ball joint connection. It can be envisaged to employ such an implant for angles of inclination not exceeding about 30°.

If need be, the implant head can be dismounted in the following manner:

In the spherical part 8, a hole is provided on the slant so as to open onto preferably, at least in part, the cavity formed by the frustum of a cone 10, for example by means of a drill or a burr 1 mm in diameter. Such a hole is represented by the dot-dash lines 16 in FIG. 1, the axis of this hole making an angle of about 30° with the longitudinal axis of the implant head 6.

An ultrasonic wave needle is introduced in this hole and the cement 15 is reduced as far as possible to a powder by the emission of ultrasonic waves.

The cement dust is eliminated as far as possible via said hole, for example by means of a jet of sterile water.

The implant head 6 is straightened (by means of a special tool) so as to return it at the minimum to a position at 15° to the longitudinal axis of the insertable member 1 or 1', preferably less than 10°. Indeed, beyond 15°, the unscrewing of the implant head 6 could deteriorate the peripheral edge of the surface of contact 4. Preferably, the implant head 6 is straightened roughly completely, then unscrewed, the connecting rod 12 coming away with the latter.

As a variant, if it is preferred that the connecting rod 12 remain on the insertable member 1 or 1', the head 6 is not completely straightened, and is then unscrewed. The rod 12 is then fully straightened and unscrewed.

Before remounting a new head—rod assembly, the surface of contact 4 and the cavity 5 of the insertable member 1 or 1' are cleaned.

The invention has been described in respect of screw-implants and blade-implants. It is well understood that it may also apply to all the other types of dental implants employed, whether these be endo-bone or juxta-bone. The juxta-bone implants are those in which the implant is fixed around the bone and not in the latter, as in the case of the endo-bone implants of the blade or screw type.

It is also possible to envisage employing the invention in the case of multi-implants for which at least two implants are used for supporting the prosthesis.

The implant head according to the invention may have any usual outer shape. It may in particular comprise circumferential grooves and/or engaging surfaces for clamping tools.

An important advantage of the invention is to make it possible to provide a standard implant that the practitioner adjusts in accordance with the case concerned. Further, the standardization of this implant simplifies its manufacture, facilitates providing supplies to the practitioner and reduces the tooling required for its mounting.

We claim:

1. A dental implant for implanting in the lower or upper jaw to serve as a support for a dental prosthesis, comprising:
    an insert member which is insertable into the bony tissue of the receiving jaw so as to ensure anchoring of the implant, said insert member including a straight part, the end of which is located so as to be substantially flush with the surface of the jaw when the insert member is inserted into the receiving jaw,
    an implant head which is detachably connected to said insert member, and onto which the dental prosthesis is mounted,
    facing ends of the insert member and the implant head form a mating ball and socket so as to form a ball joint which permits different angular orientations of the implant head relative to the insert member,
    means for ensuring immobilization of the implant head relative to the insert member in any of the permitted angular orientations,
    the straight part of the insert member having a cavity with a cylindrical portion extending concentrically with the longitudinal axis of said straight part, and the implant head also having a cavity with a cylindrical portion extending concentrically with the longitudinal axis of the implant member, these two cavities opening to face each other at the facing ends of the insert member and implant head,
    and including a connector element connectable at its ends to the insert member and the implant head in their respective cavities and having an intermediate portion extending between said ends, said intermediate portion being bendable, in the vicinity of the ball joint, the material of the connector portion being characterized by retaining its bent shape.

2. A dental implant according to claim 1, wherein the straight part of the insert member is cylindrical.

3. A dental implant according to claim 1, wherein the means for ensuring immobilization comprises a dental cement filling the cavities formed in the insert member and implant head.

4. A dental implant according to claim 3, wherein the dental cement is of the type capable of being broken up by ultrasonic waves.

5. A dental implant according to claim 1, wherein the mating surfaces of the ball and socket of the ball joint comprise a spherical part on the implant head and a mating spherical socket on the insert member, the included angle of the opening of the socket, bounded by said end of the straight part, being no more than 180°.

6. A dental implant according to claim 5, the said included angle being 180°.

7. A dental implant according to claim 5, the cavities in the insert member and implant head both being at least partially internally screw threaded in the cylindrical portions thereof, the ends of the connector element comprising satellite portions which are externally threaded complementary to said internal screw threads, such that the connection of the connector element to the insert member and implant head is by engagement of said screw threads.

8. A dental implant according to claim 7, wherein the cavity within the implant head opens into the spherical part in a widening frustoconical manner, the ball joint, the two cavities and the bendable connector element constructed and shaped to sustain an inclination of the implant head relative to the straight part of the insert member of 0° to about 30°.

9. A dental implant according to claim 1, wherein the bendable connector element is symmetrical about its point of maximum bending in the vicinity of the ball joint.

10. A dental implant according to claim 1, wherein the implant is made from pure titanium of dental grade.

11. A dental implant according to claim 1, wherein the implant is made from a titanium alloy.

12. A dental implant according to claim 1, wherein the implant is made from an aluminum alloy.

13. A dental implant according to claim 1, wherein the implant is made from a vanadium alloy.

* * * * *